United States Patent [19]

Wallstén et al.

[11] Patent Number: 4,732,152

[45] Date of Patent: Mar. 22, 1988

[54] DEVICE FOR IMPLANTATION AND A METHOD OF IMPLANTATION IN A VESSEL USING SUCH DEVICE

[75] Inventors: Hans I. Wallstén, Denens; Christian Imbert, Mézières, both of Switzerland

[73] Assignee: Medinvent S.A., Lausanne, Switzerland

[21] Appl. No.: 893,320

[22] PCT Filed: Dec. 5, 1985

[86] PCT No.: PCT/SE85/00503

§ 371 Date: Aug. 4, 1986

§ 102(e) Date: Aug. 4, 1986

[87] PCT Pub. No.: WO86/03398

PCT Pub. Date: Jun. 19, 1986

[30] Foreign Application Priority Data

Dec. 5, 1984 [SE] Sweden .................... 8406169
May 8, 1985 [SE] Sweden .................... 8502283

[51] Int. Cl.⁴ .................................. A61M 25/00
[52] U.S. Cl. .................................. 128/343; 128/344; 128/348.1; 623/1; 623/12; 604/53; 604/271
[58] Field of Search ............... 128/334 R, 334 C, 344, 128/325, 348.1, 343, 303 R, 1.2; 604/51-53, 271; 623/1, 9, 11, 12

[56] References Cited

U.S. PATENT DOCUMENTS

| 3,589,356 | 6/1971 | Silverman | 128/1.2 |
| 3,911,927 | 10/1975 | Rich et al. | |
| 4,560,374 | 12/1985 | Hammerslag | 128/344 |
| 4,665,918 | 5/1987 | Garza et al. | 128/343 |
| 4,681,110 | 7/1987 | Wiktor | 128/343 |

FOREIGN PATENT DOCUMENTS

| 2406823 | 8/1975 | Fed. Rep. of Germany | 604/271 |
| 2516640 | 10/1976 | Fed. Rep. of Germany | |
| 1456623 | 9/1966 | France | |
| 1205743 | 9/1970 | United Kingdom | 128/343 |

Primary Examiner—Dalton L. Truluck
Assistant Examiner—F. Wilkens
Attorney, Agent, or Firm—Burns, Doane, Swecker & Mathis

[57] ABSTRACT

A device and method for implantation of a prosthesis provides for insertion of the prosthesis in a location which is difficult to access. The prosthesis is held in a radially contracted state by the device. An expandable chamber within the device permits relative movements between elements of the devices as to permit the prosthesis to be inserted and radially expanded in the location.

20 Claims, 11 Drawing Figures

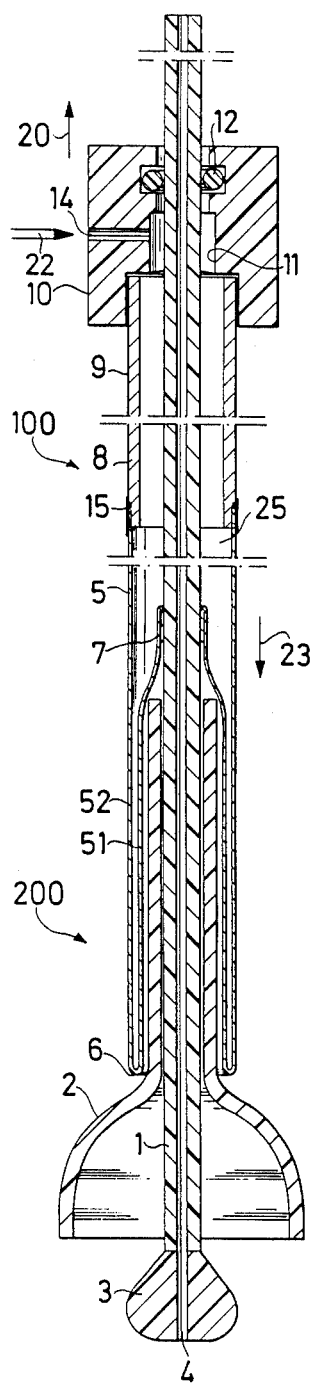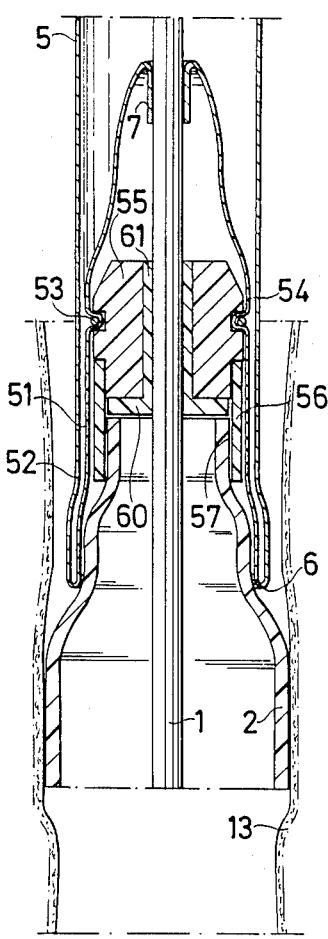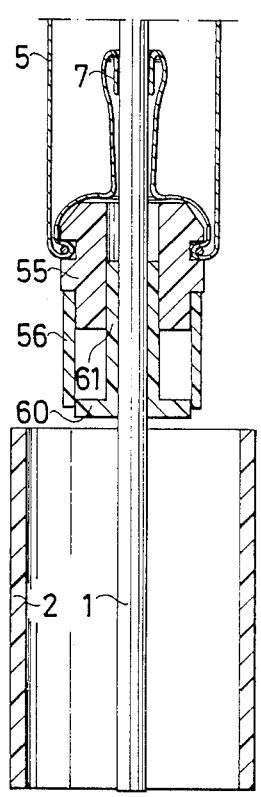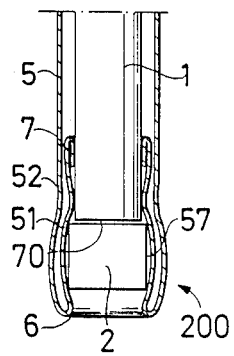

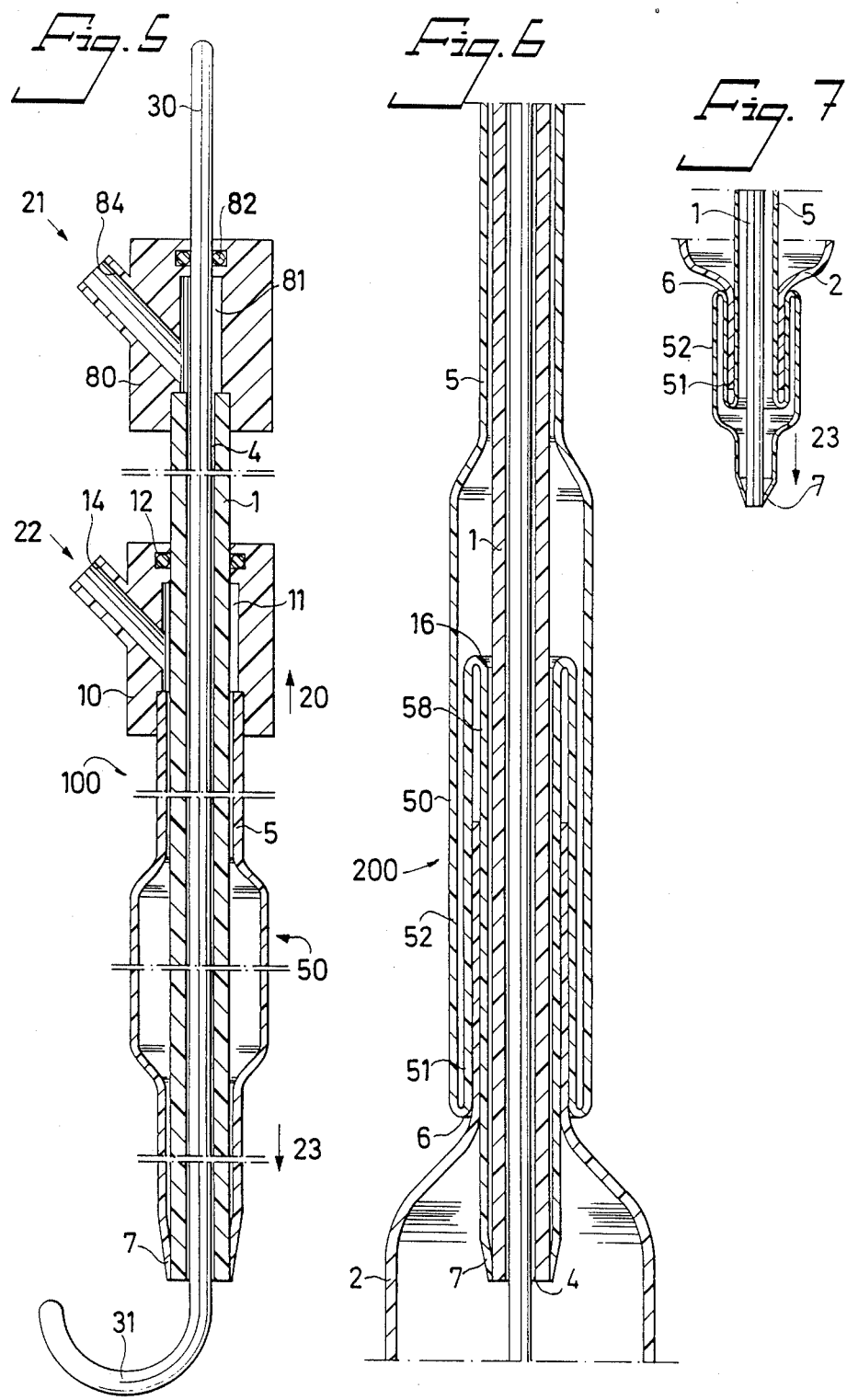

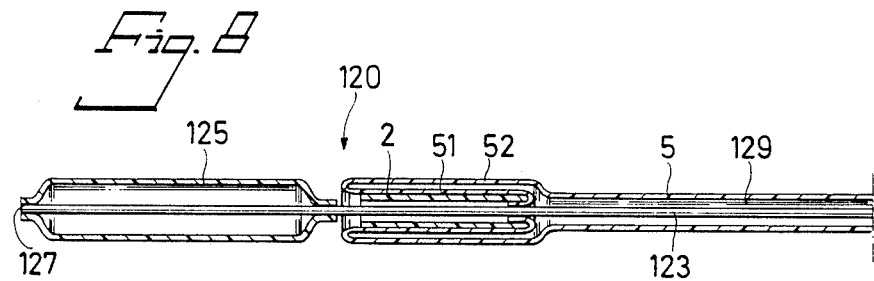
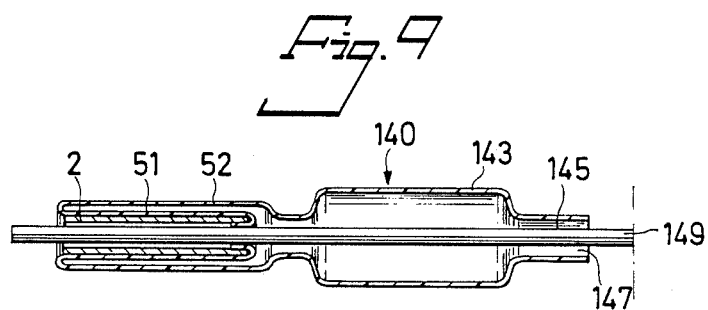
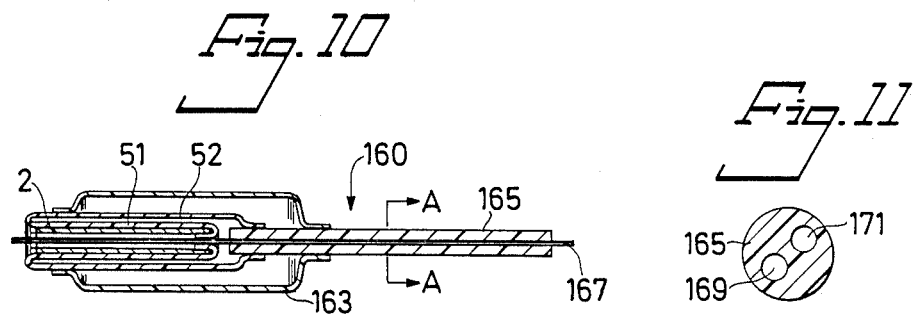
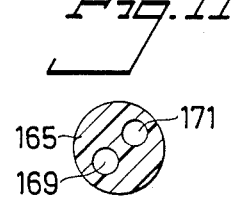

DEVICE FOR IMPLANTATION AND A METHOD OF IMPLANTATION IN A VESSEL USING SUCH DEVICE

TECHNICAL AREA

The invention relates to a device for transluminal implantation of a substantially tubular, expandable and preferably self-fixing implant, such as a graft or prosthesis.

BACKGROUND

In known devices of the type indicated above for insertion of expandable prostheses in for example a blood vessel or other narrow passage there are serious drawbacks. One such drawback consists in the fact that a gripping means embracing the prosthesis during the insertion may damage the wall of the vessel when the gripping means is widened in order to release the prosthesis. If then the gripping means is of the ejector type the friction for example between the prosthesis and the gripping means may make the ejection of the prosthesis difficult or result in damage of the prosthesis. If the prosthesis is radially compressed during the insertion to be expanded upon release the friction will be accentuated. Attempts to reduce the friction by using a lubricant exposed to the prosthesis or the wall of the passage may be inconvenient in many environments. In many cases the requirement for space of the gripping means is disturbing, and frequently the gripping means and its manoeuvring elements are of a complex nature with concomitant risk for malfunction.

The said inconveniences are particularly present when implanting a so called graft prosthesis into a vein, an artery or the like. By expandable prosthesis there is meant a tubular means forming for example a supplement to an artery, vein or the like, said prosthesis being inserted in a radially compressed state and allowed to expand radially at the location of implantation.

One object of the invention is to provide for a device of the type introductorily indicated, said device alleviating or eliminating at least some of the said inconveniences thus having the corresponding advantages in comparison with known devices.

Another advantage is to provide for a device enabling transluminal implantation of expansible prostheses of small diameter such as to be implantable by percutaneous insertion.

Still another object of the invention is to provide for a device comprising inflatable balloon means for widening the lumen before implanting the prosthesis.

Further objects and advantages of the device of the invention will be clear from the following specification or will be obvious to the skilled artisan when confronted with same.

CHARACTERIZATION OF THE INVENTION

The invention provides for a device particularly useful for transluminal implantation of an expandable self-fixing prosthesis. The device of the invention comprises in combination such prosthesis and concentric therewith a flexible probe with means for maintaining said prosthesis in a radially contracted state and for releasing same at the desired location of a lumen, characterized thereby that said means for maintaining and releasing the prosthesis comprises a flexible hose surrounding said probe, one end of said hose being connected to the probe, and the hose being folded inside itself to form a double-walled section radially surrounding the prosthesis and preferably substantially coextensive therewith, the latter being releasable by axial relative movement of the ends of the hose.

Said one end of the hose is preferably the end of the inner wall of the double-walled hose section radially seen. By this arrangement there will be no friction between the prosthesis and the hose under the release operation since the hose will be rolled off from the prosthesis.

The prosthesis is substantially tubular and is positioned to radially surround the probe, the double-walled hose section surrounding the prosthesis at the time of insertion. The probe serves the purpose of guiding the prosthesis under the insertion operation. The probe, which suitably is flexible and may consist of a suitable material, such as a polymer, can have an axially through-going channel through which fluid, for example a contrast liquid, can be introduced to the said location in the area of the forward end of the probe.

The double-walled hose section is thus arranged to radially embrace the prosthesis. The hose is preferably made from a surface-flexible and pliable material.

At least the section of the hose intended to be able to form the double-walled hose section preferably consists of polyethylene or PVC.

The double-walled hose section is thus arranged to hold a radially compressible prosthesis contracted during the insertion, the prosthesis after release thereof being allowed to expand towards normal size, to engage against the wall of the vessel.

One end surface of the probe and the double-walled hose section can be arranged to form a recess, wherein the prosthesis is received during insertion.

According to a preferred embodiment of the device the hose is leaktight, both ends of the hose are connected to the probe, and the surface of the probe adjacent to the hose between the end-connections of the hose are leaktight, whereby the hose and the probe form a chamber. In this chamber a lubricant can be introduced, particularly in the section of the hose forming the double-walled hose section, whereby the lubricant reduces friction between the interior wall and the outer wall of the double-walled hose section during release of the object. The lubricant is thus enclosed in the chamber and is exposed neither to the prosthesis, nor to the space wherein the prosthesis is released. Since the difficultly accessible location is constituted by a chosen position in a lumen, such as a vein, artery or the like in a living organism and one cannot take the risk of leakage from the chamber to expose such lubricant to said location of implantation one may instead of a lubricant introduce and pressurize a fluid, for example a blood substitute or a physiological saline solution in the chamber so that the fluid reduces the contact pressure between the walls of the hose in the double-walled hose section thereby reducing friction between the outer and the inner hose wall at relative axial movement between the two. The hose fold may, as seen in the direction of insertion of the probe, lie in front of the position, at which said one hose end is connected to the probe, so that when releasing the prosthesis by traction of the other end of the hose relative to the probe said fold moves towards said hose connection position.

The probe may at its insertion end have a bushing coaxially surrounding the probe against which the inner wall of the double-walled hose section is anchored. The bushing may be axially displacable relative to the probe and have at the front end as seen in the direction of insertion of the probe a recess, which at the time of insertion receives the end section of the prosthesis. A flange attached to the probe is arranged to form a shoulder for the end of the graft positioned in the recess, whereby when the other end of the hose is retracted the bushing and thereby the surrounding wall of the recess will be retracted from the prosthesis. The bushing and the flange hereby form an ejector device which is activated towards the end of the release operation. The wall surface of the recess radially facing the prosthesis is suitably of a material having a low friction against the prosthesis, for example Teflon. The hose is suitably anchored at the bushing in a position between the ends of the hose, whereby said one end of the hose is suitably tightly connected to the probe. The hose is preferably anchored to the bushing behind the front edge of the bushing as seen in the direction of insertion of the probe. Hereby the fold of the hose will be retracted to a position behind the free edge of the recess before further retraction of the hose moves the bushing back from the prosthesis. The other end of the hose is suitably tightly connected to the probe via a sealing device which is arranged for axial movement relative to the probe.

The front end of the probe may carry a rounded ball forming a probe head and facilitating penetration of the probe to the desired location. The ball may have a passage connected to the channel of the probe. The ball may have a diameter which is about as large as the outer diameter of the double-walled hose section when surrounding the prosthesis. The ball may be metallic to facilitate detection of the front end of the probe by means of X-rays during insertion.

The hose may be turned inside out to form a double-walled hose section surrounding the probe.

The hose may have a section of length of enlarged diameter forming the radially outer wall of the double-walled hose section.

The fold of the hose joining the walls of the double-walled hose section can be directed away from the insertion end of the probe, so that the end of the annular prosthesis facing the insertion end of the probe is lastly exposed when moving the other end of the hose.

In the latter case one may when releasing the prosthesis fixedly hold the other end of the hose and force the probe forward in its direction of insertion, the prosthesis being axially stationary relative to the environment of the probe during the release operation.

In those cases when the hose fold joining the walls of the double-walled hose section are directed forwardly in the direction of insertion of the probe one may when releasing the prosthesis hold the probe stationary and apply traction of the other end of the hose, the prosthesis being axially stationary relative to the surrounding of the probe during the release operation.

As indicated earlier in this disclosure the device according to the invention may comprise inflatable balloon means for widening the lumen before implanting the prosthesis. Such balloon means may be constituted by the outer wall of the double-walled section which when inflated insures widening before implantation.

According to another embodiment of the invention the inflatable balloon means may be positioned ahead of the double-walled section or positioned behind the double-walled section to provide for the desired widening of the vessel before the prosthesis is released at the desired location.

According to yet another embodiment of the invention the inflatable balloon means may be arranged around the double-walled section and be substantially coextensive therewith.

The invention also provides for a method of transluminal implantation of a substantially tubular expandable self-fixing prosthesis, such method comprising the steps:

(a) arranging the prosthesis in a radially contracted state around a flexible elongated probe at one end thereof and within a double-walled section of a flexible hose arranged around said probe and preferably substantially coextensive therewith said section being formed by folding one end of said hose inside itself and said end being attached to the probe;

(b) transluminally transferring the aggregate of prosthesis, probe and hose to the desired lumen location;

(c) releasing said prosthesis at said location by axial movement of the other end of the hose relative to the probe to allow radial expansion and self-fixation of the prosthesis at said location; and (d) withdrawing said probe and hose leaving the prosthesis at said lumen location.

In such method for transluminal implantation such as in case of stenosis the lumen may be widened at said location before releasing and implanting said prosthesis at said location to prevent restenosis by the prosthesis functioning as a stent. According to a preferred embodiment of the invention the method of transluminal implantation is performed percutaneously.

The invention which is defined in the appended patent claims will in the following be described in the form of non-limiting examples with reference to the appended drawings.

DRAWINGS

FIG. 1 shows diagrammatically an axial section through a device according to the invention;

FIG. 2 shows an axial section through the front part of a further development of the device according to the invention in a first position of operation;

FIG. 3 shows in an axial section a device according to FIG. 2 in a second position of operation;

FIG. 4 shows diagrammatically in an axial section a variant of the device of the invention.

FIG. 5 shows diagrammatically in an axial section another variant of the device of the invention.

FIG. 6 shows diagrammatically the device according to FIG. 5 in one position of operation;

FIG. 7 shows an alternative arrangement of the device according to FIG. 6.

FIG. 8 is a diagrammatic sideview of another embodiment of the device of the invention;

FIG. 9 is a diagrammatic sideview of yet another embodiment of the invention;

FIG. 10 is a diagrammatic sideview of still another embodiment of the invention; and FIG. 11 is a section taken along line AA in FIG. 10.

EXAMPLES OF EMBODIMENTS

In FIG. 1 there is shown a device for implantation of a so called expandable graft or prosthesis 2 in a living organism to a difficultly accessible location therein, for example a desired site of a vein or artery, graft 2 being intended to strengthen a defective section of the vein or artery.

Generally, the device includes a probe means 100 having at its insertion end means 200 to grip and carry a graft or prosthesis 2.

The device comprises an elongated flexible probe 1, preferably having an axially through-going channel 4. The tube/probe 1 is flexible and consists for example of nylon. At its front end tube 1 is provided with a rounded head 3, through which the channel 4 continues. Head 3 serves to facilitate the insertion of the device through a narrow channel. A hose 5 is at its end 7 tightly and fixedly attached to the outer surface of tube 1. Hose 5 which is soft and for example consists of polyethylene, is turned inside out to form a double-walled hose section, the inner wall of which as radially seen comprises said hose end 7. The graft 2 is a radially compressible element of tubular configuration surrounding the outer end of tube 1 and is surrounded by the double-walled section 51,52 of hose 5. By retracting the other end of hose 5 (to the right in FIG. 1 relative to tube 1) the fold 6 of the double-walled hose section 51,52 moves along the hose towards the site of attachment of end 7 of hose 5. Thereby no sliding movement takes place between graft 2 and hose wall 51. Along with the movement of fold 6 to the right in FIG. 1 graft 2 will be exposed in an axial direction and can expand to egagement against a vein or artery surface 13 (see FIG. 2). The other end of hose 5 is tightly connected to the outer surface of tube 1. Hose 5 is coaxially connected to a flexible maneuvering tube consisting of a helix spring 8 of stainless steel, spring 8 being exteriorly covered by a removable tight enclosure of for example polyvinylchloride. PVC-enclosure 9 is tightly connected to the polyethylene tube by means of a joint 15. A bushing 10 surrounds tube 1 and is rigidly connected to the spring 8 and tightly connected to enclosure 9. The other end of the bushing has an O-ring seal 12 sealing against the outer surface of tube 1. Tube 1, hose 5, spring enclosure 9, bushing 10 and seal 12 thus form a closed chamber 25. Bushing 10 has a bore 14 extending through the wall of the bushing and forming a channel, through which a fluid 22, such as physilogical saline solution, blood substitute, air or the like, can be introduced and pressurized in space 25. Hereby fluid 22 can penetrate in between hose walls 51,52 and separate same so that they at substantially reduced friction can move axially relative to each other.

Channel 4 of tube 1 can be used to introduce a contrast fluid 21 to the area around the front end of the device so that the position of the device may be easily detected for example using X-ray technique.

To release graft 2 the operator can using one hand hold the aft end of tube 1 and using the other hand retract bushing 10 in the direction of arrow 20, the fold 6 of hose 5 being retracted so as to release graft 2.

In FIG. 1 the direction of insertion of the device is indicated by arrow 23.

If graft 2 consists of a graft of the type comprising a tubular sleeve having a helix-shaped wire reinforcement there is little risk that the reinforcing wire ends at the aft end of graft 2 form punctures in hose 5 in connection with releasing the aft end of graft 2. In order to eliminate this risk there is suggested a further development of the invention, the device of the invention being designed in the manner which is clear from FIGS. 2 and 3.

In FIGS. 2 and 3 the details corresponding to those of FIG. 1 are provided with the same reference numerals.

Tube 1 is at its front part provided with an annular flange 60 which has a hub 61 fixedly connected against the outer surface of tube 1. A bushing 55 surrounds hub 61 and is controlled by same for axial movement relative to flange 60. Flange 60 constitutes a stop for bushing 55 in the direction of insertion of device 23. Bushing 55 has at its front end a fixedly connected tube section 56 of a material of low friction extending towards graft 2 and preferably consisting of Teflon ®. When bushing 55 is in its forward position (FIG. 2) tube section 56 and flange 60 form a recess 57 receiving the aft end of the radially compressed graft 2. The inner wall 51 of the double-walled hose section is anchored against the periphery of bushing 55. The anchorage consists of a circumferential recess 54 in the outer wall of bushing 55. The surrounding binding 53 clamps hose wall 51 in the recess. When hose 5 is retracted so as to move fold 6 to the right fold 6 will move on over tube section 56 and up to the circumferential recess 54 of the bushing. Continued retraction of hose 5 then results in retraction of bushing 55 and thereby Teflon ® tube section 56 relative to flange 56, the aft end of graft 2 being exposed and being radially expandable without risk of puncture of hose 5.

FIG. 4 illustrates the front end of an alternative device according to the invention. The device includes a flexible elongated probe 1 coaxially surrounded by a hose 5, one end 7 of which is fixedly and tightly connected to the outer surface of probe 1. Hose 5 is turned inside out to form a double-walled hose section 51,52 extending forwardly of the front end surface 70 of probe 1. End surface 70 and the double-walled hose section 51,52 form a recess receiving graft 2. Said graft 2 is released by retracting the other end of hose 5 (to the right in FIG. 4).

FIGS. 5 and 6 show an example of the device wherein the details corresponding to those of the preceding figures have the same reference numerals. In addition to this FIG. 5 shows that hose 5 has a length section 50 of enlarged diameter. When hose 5 is turned inside out to a double-walled section 51,52 surrounding the tubular graft 2 the diameter enlarged hose section is formed as the outer wall 52 in the double-walled hose section 51,52 (FIG. 6).

By this arrangement hose 5 need not be radially expanded to be able to receive graft 2 between the double-walled hose section 51,52 and the hose section surrounding probe 1 and lying radially inwardly thereof.

In FIGS. 5 and 6 the one front end of hose 5 is shown fixedly connected to the front end of the probe at 7, the fold 6 as seen in the direction 23 of insertion of the probe being intended to lie behind the position 7 of connection, whereby fold 6 moves away from the position when the graft is released by traction of the other end of hose 5 relative to the probe 1.

In FIG. 1 the graft 2 is shown in direct engagement against probe 1, whereas in FIGS. 5 and 6 the graft surrounds a hose section 58 directly surrounding probe 1.

The fold 16 between the hose sections 58 and 51 will normally lie relatively still relative probe 1, whereby fold 16 may be said to functionally constitute the position, at which the front end of hose 5 is connected to probe 1.

In FIG. 6 there is shown the double-walled section 51,52 arranged so that fold 6 is facing the front end of the probe.

It should be noted, however, that section 51,52 may be reversed so that fold 6 faces away from the front end of the probe, as shown in FIG. 7. In this case graft 2 can be released starting at the aft end of the graft. This possibility is of interest when a graft shall be implanted in for example an artery in which the flow of blood is in a direction opposite to the direction of insertion of the probe.

In this way the risk will be avoided which is present in the arrangement according to FIG. 6, residing in the fact that the flow of blood may fold the end of the graft which is first exposed and expands.

It is usually suitable to see to it that the graft is stationary relative to the surrounding during the release operation. In the arrangements according to for example FIGS. 1 and 6 this state can be obtained by holding probe 1 stationary relative to the surrounding and the aft end of hose being retracted during the release operation.

In the arrangement according to FIG. 7 the said state will be obtained by maintaining the aft end of hose stationary and moving probe 1 forwardly in its direction of insertion.

In FIG. 5 there is shown the aft end of probe 1 attached in a housing 80 having a chamber 81 communicating with channel 4 of probe 1. A channel 84 extends through the wall of housing 80 and communicates with chamber 81 to admit introduction of the fluid 21 to the area of the front end of the probe.

Housing 80 further has an aperture with a seal 82 of O-ring type.

A rod 30 extends through channel 4 of probe 1, chamber 81 of housing 80 and sealing 82, said rod 30 being tightly surrounded by seal 82. The front end section 31 of rod 30 is bent over about half a turn with a radius of curvature which for example approximately corresponds to the diameter of probe 1.

Rod 30 is suitably elastic in order that its front end section during insertion of the probe shall be able to bend the front part of the probe. In this connection rod 30 can be retracted so that end section 31 will be drawn into the front part of probe 1 while bending same in response to the combined effect of the elastic resistance to bending of probe 1 and end section 31. The extent of bending of the probe end part can then be varied by turning rod 30, and the angle of deflection of the probe end part can be selected by changing the length of the section of the bent rod section 31 which is retracted into probe 1.

FIGS. 8 to 11 of the appended drawings relate to embodiments of the device of the invention including in addition to the feature of enabling implantation of an expandable graft or prosthesis also means for dilatation of a stenosis in a vessel or lumen before implanting a supporting graft serving as a stent to prevent restenosis.

FIG. 8 is a diagrammatic sideview of such an embodiment of the device of the invention. The device comprises a central tubing 123 surrounded by a flexible hose 5 including the double-walled section 51,52. The radially compressed graft 2 is as described before positioned inside the double-walled section 51,52 and surrounding the central tubing 123.

At the front end of central tubing 123 there is arranged a dilatation balloon 125 sealingly attached at both ends to the central tubing 123.

While not shown in detail in the drawing balloon 125 can be pressurized separately from the double-walled section 51,52 by pressurizing the central passage 127 of tubing 123. The double-walled section 51,52 can be pressurized by introducing a pressure medium in the annular space 129 formed between tubing 123 and the surrounding hose 5.

In operation the device shown in FIG. 8 functions briefly as follows.

After insertion of the device generally designated 120 into the desired location of for example a blood vessel, balloon 125 is inflated by separate pressurization of same. This inflation of the balloon has for a purpose to widen the lumen at the location of the stenosis and where graft 2 is later to be implanted.

After widening the lumen at the desired location balloon 125 is deflated and the device 120 moved forward so that the double-walled section 51,52 thereof takes the proper position in the vessel. By relative movement between central tubing 123 and hose 5 in an axial direction graft 2 can now be released at the desired location in the vessel to provide for permanent reinforcement of the vessel whereby for example restenosis can be avoided. After the implantation the device 120 is then removed from the vessel.

The embodiment shown in FIG. 9 performs the same functions as that of FIG. 8, but the dilation balloon is positioned behind the double-walled section 51,52. In this embodiment the device is generally designated 140 and the inflation of the double-walled section 51,52 to avoid friction is performed using the same pressure medium as used for inflating balloon 143 due to the communicating passage therebetween. The function of the device of FIG. 9 is otherwise the same as that of FIG. 8 the same advantages being obtained by providing a central tubing or probe 149 and introducing a fluid pressure medium in the annular space 147 between an outside area 145 of the tube 149 and the interior of the balloon 143.

In FIG. 10 there is shown an embodiment where balloon 163 is arranged so as to surround the double-walled section 51,52. This embodiment designated 160 contains a central wire or thread 167 surrounded by a hose 165. Surrounding the hose 165 there is arranged a balloon 163 sealingly attached to the hose at the aft end and to the front part of the outer wall 52.

To provide for separate pressurization of the balloon and the double-walled section 51,52 there is arranged within hose 165 two internal passages 169,171, as shown in FIG. 11 in an enlarged cross section. Passage 169 can be used for accomodating the central wire 167 and for pressurizing the double-walled section 51,52 to reduce friction. Passage 171 can be used for pressurizing the dilatation balloon 163 separately from the double-walled section 51,52. It is, of course, possible to arrange for three internal passages within hose 165, two for individual pressurization and one for a central guidewire.

The function of the device shown in FIG 10 is the same as that of the devices shown in FIGS. 8 and 9 with the difference that no axial displacement of the device has to be performed after widening the lumen using the balloon 163 since the position of widening the lumen is juxtaposed to the graft or prosthesis 2 accomodated within the double-walled section 51,52.

In the above specific examples of devices according to the invention have been described. It is to be noted that modifications can be made to the examples shown. Thus, instead of introducing and pressurizing a fluid 22 in space 25 one can arrange a lubricant in chamber 25, particularly in the area between the walls 51, 52 of the double-walled hose section in order to reduce the friction between same.

With reference to FIG. 1 it is further to be noted that details 8, 9, 10, 11, 12, 14, 15 can be omitted if the hose 5 or the traction means attached thereto extend to the area of the aft end of probe 1 so that the retracting movement of hose 5 can be controlled from an accessible location. If hose 5 consists of a material having low friction against itself one may optionally dispense with lubricant in or a fluid pressurization of the space between the walls 51,52 of the double-walled hose section.

The invention provides for a new and highly versatile device for the implantation of prostheses or grafts of the radially expandable self-fixing type. The new device enables implantation of grafts of almost any diameter within the range of interest, which extends from small diameters of just one or a few millimeters up to diameters of several centimeters. The design of the device of the invention particularly enables so called percutaneous transluminal peripheral as well as coronary angioplasty offering in addition to the known balloon dilatation feature also the possibility of implanting a graft or prosthesis after widening the lumen. It is for instance known that conventional percutaneous transluminal coronary angioplasty using only the balloon means frequently results in restenosis at the angioplasty site usually calling for elective coronary bypass graft surgery, which is a much more complicated and risky procedure. Using the small diameter version of the device of the invention, the diameter being as small as a few millimeters, no surgical operation will be necessary for implanting a graft in a vessel since simple percutaneous insertion can be resorted to.

The prosthesis used in the device of this invention can be of any type as long as it is radially expandable to provide for radial expansion and self-fixation when released in a vessel or other tract. A particularly preferred prosthesis or graft is described in published British patent specification No. 8411519 the disclosure of which is incorporated herein by reference. This prosthesis or graft comprises a flexible tubular body which is composed of several individual rigid but flexible thread elements each of which extends in helix configuration with the centerline of the body as a common axis, a number of elements having the same direction of winding but being axially displaced relative to each other crossing a number of elements also axially displaced relative to each other but having the opposite direction of winding. The diameter of such prosthesis or graft is variable by axial movement of the ends of the body relative to each other.

According to a modification of the invention the prosthesis used in the device as disclosed herein can be formed from a so called recovery metal, such as a titanium-nickel alloy possessing a mechanical "memory". In such modification the prosthesis in a radially contracted state will maintain such state by cooling before insertion surrounded by the probe of the device. Upon implantation after release at the desired location the device and the prosthesis may then be heated by introducing a heating medium into a channel extending through the probe, such heating resulting in expansion of the prosthesis by initiating its recovery ability. As examples of suitable alloys for use in such prosthesis possessing mechanical memory there may be mentioned the nickel-based alloys described in U.S. Pat. No. 3,174,851, the disclosure of which is incorporated herein by reference. The function of the device incorporating such prosthesis is in other respects the same as described in connection with the other embodiments disclosed herein.

We claim:

1. A device for implantation by insertion in a difficultly accessible location of a substantially tubular, radially expandable prosthesis, including in combination said radially expandable prosthesis surrounding and concentric with a flexible probe and means for maintaining said prosthesis in a radially contracted state and for releasing said expandable prosthesis in the difficultly accessible location, wherein said means for maintaining and releasing the prosthesis comprises a hose concentrically surrounding said probe with one end of said hose being connected to the probe, the hose being folded inside itself, a double-walled section of said hose formed by said hose being folded inside itself, said double-walled section radially surrounding the prosthesis, a fluid-tight chamber provided between and defined by said probe and said hose, means for introducing and pressurizing a fluid in said chamber to reduce contact pressure and friction between said double-walled section of the hose, the prosthesis being released from the hose by axial relative movement of said one end of the hose with respect to an opposite end of said hose, said opposite end of said hose connected to an element of said device.

2. A device according to claim 1, characterized thereby that one end surface (70) of the probe and the double-walled hose section (51,52) form a recess (57) wherein the object (2) is received during insertion.

3. A device according to claim 1, characterized thereby that the hose fold (6) of the double-walled hose section (51,52), as seen in the direction (23) of the transluminal insertion of the device, lies in front of the position, at which said one hose end (7) is connected to the probe, whereby prosthesis (2) can be released by traction of the other end of the hose, the fold (6) moving along prosthesis (2) towards said hose connection position.

4. A device according to claim 1, characterized thereby that the hose fold (6) of the double-walled hose section (51,52), as seen in the direction (23) of the transluminal insertion of the device, lies behind the position, at which said one hose end (7) is connected to the probe, whereby prosthesis (2) can be released by traction of the other end of the hose, the fold (6) moving along prosthesis (2) towards said hose connection position.

5. A device according to claim 1, characterized thereby that the probe (1) at its front end has a bushing (55) coaxially surrounding the probe against which the inner wall (51) of the double-walled hose section is anchored, that the bushing is axially displacable relative to the probe, that the bushing at the front end thereof as seen in the direction (23) of the transluminal insertion of the device, has a recess (57), which at the time of insertion receives the end of prosthesis (2), that a flange (60) is attached to the probe (1) and arranged to form a shoulder for the end of prosthesis (2) positioned in the recess, whereby when the other end of the hose is retracted the bushing (55) and thereby the surrounding wall (56) of the recess are retracted from the prosthesis (2).

6. A device according to claim 1, characterized thereby that the probe (1) has at least one axially throughgoing channel (4).

7. A device according to claim 1, characterized thereby that the other end of the hose (5) is tightly connected to the probe (1) by sealing means (10,12) permitting axial movement relative to the probe (1).

8. A device according to claim 1, characterized thereby that a lubricant is arranged on the inside of hose (5) in its double-walled section (51,52).

9. A device according to claim 1, characterized thereby that the outer wall of the double-walled section is inflatable to ensure widening of the lumen before implanting the prosthesis.

10. A device according to claim 1, characterized by inflatable balloon means positioned ahead of the double-walled section for widening the lumen before implanting the prosthesis.

11. A device according to claim 1, characterized by inflatable balloon means arranged around the double-walled section and substantially coextensive therewith, said means preferably being independently operable for widening the lumen before implanting the prosthesis.

12. A device according to claim 1, characterized by inflatable balloon means positioned behind the double-walled section for widening the lumen before implanting the prosthesis.

13. A device according to claim 1, characterized thereby that the prosthesis comprises a flexible tubular body which is composed of several individual rigid but flexible thread elements each of which extends in helix configuration with the centerline of the body as a common axis, a number of elements having the same direction of winding but being axially displaced relative to each other crossing a number of elements also axially displaced relative to each other but having the opposite direction of winding.

14. A method of implantation in a vessel of a substantially tubular, radially expandable prosthesis, comprising the steps of:
(a) radially contracting the radially expandable prosthesis around one end of a flexible elongated probe and within a double-walled section of a hose radially surrounding said probe;
(b) forming said double walled section by folding one end of said hose inside itself, said end being attached to said probe;
(c) positioning a combination of said prosthesis, said probe and said hose at a desired location in said vessel;
(d) providing a chamber defined between said hose and said probe;
(e) pressurizing said chamber to friction between walls of said double-walled section;
(f) releasing said prosthesis at said location by axial movement of an opposite end of the hose relative to the probe so as to allow radial expansion and engagement of the prosthesis with wall sections of said vessel of said location; and
(g) withdrawing said probe and said hose from said vessel location while leaving said prosthesis at said vessel location.

15. The method of claim 14, comprising the step of widening the vessel at said location before implanting said prosthesis thereat.

16. The method of claim 14, wherein the implantation is performed by percutaneous transluminal implantation.

17. A device according to claim 2, characterized thereby that the hose is leaktight, that both ends of the hose are tightly connected to the probe (1) and that the surface of the probe adjacent to the hose is leaktight between the endconnections of the hose, whereby the hose and the probe form a chamber (25) and that means (14, 22) are arranged for pressurizing a fluid in chamber (25), whereby the fluid reduces the contact pressure between the hose walls of the double-walled section (51, 52) thereby reducing the friction between the outer hose wall (51) and the inner hose wall (51) at axial relative movement between same.

18. A device according to claim 2, characterized thereby that the hose fold (6) of the double-walled hose section (51, 52), as seen in the direction (23) of the transluminal insertion of the device, lies in front of the position, at which said one hose end (7) is connected to the probe, whereby prosthesis (2) can be released by traction of the other end of the hose, the fold (6) moving along prosthesis (2) towards said hose connection position.

19. A device according to claim 3, characterized thereby that the hose fold (6) of the double-walled hose section (51,52) as seen in the direction (23) of the transluminal insertion of the device, lies in front of the position, at which said one hose end (7) is connected to the probe, whereby prosthesis (2) can be released by traction of the other end of the hose, the fold (6) moving along prosthesis (2) towards said hose connection position.

20. The method of claim 15, wherein the implantation is performed by percutaneous transluminal implantation.

* * * * *